United States Patent
Herrmann et al.

(10) Patent No.: US 9,615,812 B2
(45) Date of Patent: Apr. 11, 2017

(54) CALIBRATION OF IMAGERS WITH DYNAMIC BEAM SHAPERS

(71) Applicant: KONINKLIJKE PHILIPS N.V., Eindhoven (NL)

(72) Inventors: Christoph Herrmann, Aachen (DE); Bernd Menser, Hauset (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 7 days.

(21) Appl. No.: 14/893,963

(22) PCT Filed: Jun. 19, 2014

(86) PCT No.: PCT/EP2014/062942
§ 371 (c)(1),
(2) Date: Nov. 25, 2015

(87) PCT Pub. No.: WO2014/202720
PCT Pub. Date: Dec. 24, 2014

(65) Prior Publication Data
US 2016/0113617 A1 Apr. 28, 2016

(30) Foreign Application Priority Data

Jun. 19, 2013 (EP) .................................. 13172609

(51) Int. Cl.
*A61B 6/00* (2006.01)
*A61B 6/03* (2006.01)

(52) U.S. Cl.
CPC .............. *A61B 6/585* (2013.01); *A61B 6/032* (2013.01); *A61B 6/4035* (2013.01); *A61B 6/42* (2013.01); *A61B 6/544* (2013.01); *A61B 6/545* (2013.01); *A61B 6/582* (2013.01); *A61B 6/4441* (2013.01)

(58) Field of Classification Search
CPC .......... G21K 1/06; G21K 1/062; G21K 1/067; G21K 2207/005
See application file for complete search history.

(56) References Cited

U.S. PATENT DOCUMENTS

| 4,181,858 A | 1/1980 | Moore |
| 6,426,999 B2 | 7/2002 | Prins |
| 6,430,265 B2 | 8/2002 | Prins et al. |
| 6,438,211 B1 | 8/2002 | Weekamp et al. |
| 6,453,012 B2 | 9/2002 | Herbert |

(Continued)

FOREIGN PATENT DOCUMENTS

| WO | 99/38172 | 7/1999 |
| WO | 2009/063353 | 5/2009 |
| WO | 2012/042484 | 4/2012 |

*Primary Examiner* — Hoon Song

(57) ABSTRACT

Calibration methods and related calibration controllers (CC) for calibrating imaging apparatuses (102) such as a 3D computed tomography imager or a 2D x-ray imager. The imaging apparatuses (102) are equipped with a dynamic beam shaper (RF). The dynamic beam shaper (RF) allows adapting the energy profile of a radiation beam (PR) used in the imaging apparatuses (102) to a shape of an object (PAT) to be imaged. A plurality of gain images are acquired in dependence on a shape of the object and the view along which the gain images are acquired or a target gain image is synthesized from a plurality of basis gain images (BGI).

13 Claims, 5 Drawing Sheets

(56) References Cited

U.S. PATENT DOCUMENTS

| | | | |
|---|---|---|---|
| 6,453,013 B2 * | 9/2002 | Prins | G21K 1/10 378/156 |
| 6,990,171 B2 * | 1/2006 | Toth | A61B 6/032 378/158 |
| 7,046,756 B2 | 5/2006 | Hoffman | |
| 7,308,073 B2 | 12/2007 | Tkaczyk et al. | |
| 7,616,737 B2 | 11/2009 | Kuiper et al. | |
| 7,630,477 B2 | 12/2009 | Toth et al. | |
| 7,889,901 B2 * | 2/2011 | Bontus | G06T 11/006 378/4 |
| 2013/0010917 A1 * | 1/2013 | Thibault | G06T 11/006 378/4 |

* cited by examiner

CALIBRATION OF IMAGERS WITH DYNAMIC BEAM SHAPERS

CROSS REFERENCE TO RELATED APPLICATIONS

This application is a national filing of PCT application Serial No. PCT/EP2014/062942, filed Jun. 19, 2014, published as WO 2014/202720 A1 on Dec. 24, 2014, which claims the benefit of European Application Number 13172609.3 filed Jun. 19, 2013, which is incorporated herein by reference.

FIELD OF THE INVENTION

The present invention relates to calibration methods, to imagers, to calibration controllers, to imaging systems, to a computer program element, and to a computer readable medium.

BACKGROUND OF THE INVENTION

Most of today's CT (computed tomography) scanners use beam shapers, often called bowtie filters, to adapt the intensity profile of the scanner's x-ray (that is incident on a patient) to the thickness profile of the patient to be imaged. The so adapted, in general spatially non-uniform, x-ray profile helps secure a number of advantages: less patient dose, less x-ray scatter, more homogeneous image quality, and reduction of the dynamic range requirements for the scanner's detector by using lower intensity in certain parts of the beam, especially in those parts in direct irradiation areas. Some beam shapers allow selection from a (usually very limited) set of available filter bodies that are based on a rough patient classification (e.g. child, adult, etc).

There are also "dynamic" beam shaping devices that afford a high degree of adaptability of their filter bodies to individual body shapes. Examples of such filters are described in Applicant's WO 2013/001386 or U.S. Pat. No. 6,453,013. However it has turned out that calibration procedures (that is, the acquisition of gain correction images or "air scans") for imagers having such (highly) adaptable beam shapers are remarkably cumbersome.

SUMMARY OF THE INVENTION

There may therefore be a need for an alternative calibration method and related controller to facilitate calibration of imagers having dynamic beam shapers.

The object of the present invention is solved by the subject matter of the independent claims where further embodiments are incorporated in the dependent claims. It should be noted that the following described aspect of the invention equally apply to the imagers, to the calibration controllers, to the imaging systems, to the computer program element, and to a computer readable medium.

According to one aspect of the invention there is provided a calibration method for an imager having an adjustable filter arranged between a radiation source of the imager and a detector of the imager, the filter suitable to effect, by adjustment of the filter's setting, different non-homogenous intensity profiles of a radiation beam generated by the source before passage of said beam through an object to be imaged. The calibration method comprises:

adjusting the filter for a plurality of different basis filter settings, one at a time;

acquiring at the imager's detector a plurality of basis gain images, at least one gain image for each of the different filter settings; and synthesizing a target gain image from the one or more of the plurality of gain images. The target gain image can then be used for an instant image acquisition of an object. Because the target image is "artificially" synthesized from the set of previously recorded basis gain images, there is no interruption of clinical imaging work flow because an intermediate calibration step is no longer needed. Rather, the target gain image, for a required (target) filter setting in a forthcoming imaging of the instant patient, is generated, i.e., synthesized, "on-the-fly". The synthesized target gain image can be gotten without using the imager to actually record, in an "air scan", the needed target gain image.

According to one embodiment, the synthesizing step includes forming a linear combination from the one or more of plurality of basis gain images. In other words, the target gain image can be composed from the basis gain images by i) superimposing the (or a suitable selection of) basis gain images and by ii) scaling up or down the respective, local basis image attenuation strength (as recorded in each of the basis images) to fit locally the attenuation strength required by the target attenuator setting that is to be used for an image acquisition of an object.

In one embodiment, the synthesizing step includes a beam hardening compensation or correction step to ensure that the superposition of the basis gain image (that is, their line integrals) is applicable also for polychromatic x-ray beam exposures.

According to one embodiment, an attenuation profile of each gain image in the plurality of gain images is caused by a respective, locally restricted pre-attenuation of the adjustable filter. In one embodiment, the attenuation profile is essentially a different single-dip profile (except for possible ripples caused by noise) for each basis gain image. For instance, according to one embodiment, the filter includes a plurality of individually addressable filter elements to effect an essentially pointwise or at least localized pre-attenuation action of the beam, wherein the single dip attenuation profiles each correspond to (or are associated with) a respective one of the filter elements. In other words, the single-dip profile is caused by a local attenuation action of the adjustable filter when only one filter element is activated for attenuation. For instance, in one embodiment, the filter is formed from a matrix of liquid filled tubelets each defining a filter element and a filter action is locally defined by which one of the tubelets is actually filled at all and the respective strength is defined by the height of the respective fill level. That is, each basis image records the (local) attenuation action (at a defined strength) of only a single filter element. It is envisaged herein, that each filter element is aligned with the X-ray tube (in particular with the central ray of same) during recording for the respective basis gain image to minimize the extent of x-ray shadows (or penumbra). However, in some embodiment the filter body width is so chosen, that the effect of the x-ray shadows can be neglected.

According to one embodiment, the linear combination involves weights, each weight representing the individual attenuation strength of a respective one of the filter elements. For instance, in the tubelets embodiment, the weights indicate the required fill level at the respective filter elements or tubelets.

In one embodiment there are at least one basis image per filter element to so ensure that any required filter pattern can be obtained by superposition. According to one embodiment there are exactly as many basis images as there are filter elements, each basis image recoding the attenuation at a pre-set (user determined) level of a (respective) single one of the filter elements thus resulting in the single dip profile (corresponding to a single peak profile after conversion into the corresponding line integral by negative logarithmic scaling). However, the single dip profile is but one embodiment and other "attenuation patterns" are also envisaged that involve basis gain images with different profiles, so long as the required attenuation pattern for an instant object to be imaged is combinable. For instance, if the overall shape of the object part is known in sufficient approximation, this knowledge can be used as a constraint on the profile shape of the gain images. For instance, if, due to the object's symmetry, there is thickness variation in merely one direction, then the base filter settings can be so chosen that the basis gain image profiles vary only in said direction. This allows defining a basis with fewer basis gain images rather than recording a gain image for each and every filter element.

In another embodiment, there are, however, a plurality of associated basis gain images per filter element, each one being a recording at a different level of attenuation. Having gain images for different attenuation strengths per locale, allows better accounting for the different extents of the respective x-ray shadows caused by the respective filter element when operating with different attenuation strengths. For instance, the different attenuation strengths are achieved in some embodiments by "stacking up" or layering more or less layers of attenuating filter material. In the tubelet filter embodiment, different attenuation strengths correspond to different fill levels (filter element thickness or "height") and thus different x-ray shadows will result. Having different gain images for different fill level heights per filter element allows accounting for said x-ray shadows (or penumbra).

It will appreciated, that the "tubelet" embodiment for the adjustable filter is used as an exemplary embodiment herein for a highly shape adaptive filter and the proposed method may be applied also to other (solid)-mechanical examples of such filters that can be controlled to effect essentially localized (pointwise) attenuation.

The basis gain images caused by the respective basis filter setting or configuration are acquired (measured) preferably in an "offline" calibration procedure. Thus, there is no need for intermediate calibration acquisitions for each patient scan. The proposed method may be used for 3D CT but is suitable also for calibration in 2D radiography contexts.

According to one embodiment, the step of synthesizing the target gain image is executed in response to receiving a shape specification of an object to be imaged. The shape specification may be supplied by a suitable shape detector (such as a 3D camera) that senses the shape of an instant patient or may be supplied by the user specifying the body shape from a number or pre-stored body types.

According to a further aspect of the invention there is provided a calibration method for an imager having an adjustable filter arranged between a radiation source of the imager and a detector of the imager, the filter suitable to effect, by adjustment of the filter's setting, different non-homogenous intensity profiles of a radiation beam generated by the source before passage of said beam through an object to be imaged. The method comprises:

adjusting the filter to a plurality of different filter settings, one at a time;

acquiring at the imager's detector a plurality of gain images, at least one gain image for each of the different filter settings, wherein the imager's x-ray source is rotatable about an examination region, wherein each of the gain images are acquired at different views with the filter setting adjusted in dependence on the different views.

According to one embodiment, the method further comprises the step of receiving at least one specification of a shape of the object, wherein the filter setting adjustment step is in dependence on the received object shape specification.

According to one embodiment, the method further comprises the step of optically scanning the object to obtain the received object shape specification. "Optically scanning" as used herein is to mean in some embodiments that non-ionizing radiation is used to interrogate for the object's shape but there are also embodiments envisaged where a 3D scout scan is done with a very low dosage. The shape specification may be in the form of 2D depth images (2D thickness profiles) or in the form of a 1D thickness profile. The shape specification may be supplied by a 3D optical camera or by a 2D scout scan together with a suitable 3D patient model or any other suitable means. The optical scanning step may also be used in connection with the previous method according to the first aspect, when, during the actual imaging run, the filter is adjusted for the target setting in response to the sensed patient shape. The optical scanner may be arranged to rotate around the object in manner similar to the rotation of the imager's x-ray source but there are embodiments envisaged where the optical scanner is fixed and the shape specification for the different views are derived from one or more shape specifying images acquired from a fixed position relative to the object.

According to one embodiment, the different filter settings are pre-stored in a memory (database) and wherein the adjustment step includes selecting for each view a filter setting from said pre-stored filter settings, each pre-stored filter setting associated with a respective object shape and view on said shape, the selection being dependent on the received object shape specification. In other words, in this embodiment the filter settings is not adapted to an actual measurement of the body shape of the instant patient but a fitting pre-stored setting is chosen instead. The pre-stored gain filter settings can then be used to acquire the gain images at a convenient time slot to accommodate existing work flow constraints.

According to one embodiment, it is the detector gain images that are stored in the same or database/repository (with or without their respective filter settings that were used to record said gain images). The gain images are pre-stored and can be used for a future object image acquisition: one of the stored gain images is then loaded into the imaging system that corresponds best to the received shape of the object. The loaded gain image can then be applied to a currently acquired object image in the image generation algorithm, for instance in CT image reconstruction. The method allows to "decouple in time" the gain image acquisition from the actual patient imaging. The gain image acquisition may be scheduled for execution on a regular bases, such as one per day (for instance in an early morning slot prior to the patient imaging session) or even less frequently such as once per week or once per month.

According to one embodiment, the optically scanning step and the gain image acquiring step is synchronized with the different view. This can be done in different ways for flexible integration into existing work flow constraints.

The methods proposed herein can be used with of photon counting radiation detectors based on direct conversion detectors or with energy integrating detectors. The imagers as envisaged herein are either 3D CT (computed tomography) scanners or 2D x-ray apparatuses for instance C-arm as used during interventions. However, the methods may also be put to good use in contexts other than medical, are also envisaged, for example in medical imaging systems, instrument for scientific purposes, or security technology.

In either one of the two calibration methods according to the two aspects, when a shape detector for supplying the shape specifications is used, the shape detector may be installed on the imager's gantry or C-arm close to the X-ray tube for instance. In this embodiment, in the method according to the first aspect, the gain images and the shape specification are acquired in turn for each view or, in the method according to the first aspect, the target gain image can be synthesized in response to acquisition of the shape specification at a view and the imaging of the object can then commence thereafter at said view.

According to a further aspect there is provided an imager that operates to acquire an image of the object, wherein the imager's image generation algorithm applies one or more of the plurality of gain images or applies the target gain image.

According to a further aspect there is provided a calibration controller for an imager configured to carry out the method steps according to the first or second aspect.

According to a further aspect there is provided a computer program element for controlling the calibration controller, the computer program element, when being executed by a processing unit, adapted to perform the method steps according to the first or second aspect.

According to a further aspect there is provided a computer readable medium having stored thereon said program element.

DEFINITIONS

"(pre-)Filter/beam shaper" as used herein is a pre-filter that operates to pre-attenuate the x-ray beam supplied by the radiation source before the x-ray beam is incident on the object/detector. The primary goal of the pre-filter is to modulate intensity of the beam although there are also changes in the spectrum and of the mean energy of the beam. Preferably, the filter can be operated so that individually addressable filter elements can be spatially re-arranged or otherwise activated to effect a plurality of different energy intensity profiles in the beam that are tailored to the shape of the object (patient, item of baggage etc) of interest. For instance, given a generally ellipse shaped cross-sectional shape of the object (as can be expected for the human torso), the pre-filter provides an attenuation pattern wherein (almost) no pre-attenuation for the central beam, (where typically the most of the object attenuation occurs), while provides a relatively high pre-attenuation of the incident x-ray beam at the periphery. Other spatial attenuation patterns are also envisaged as required by the shape of the respective body part of interest.

"Gain image": is an image acquired whilst no object to be imaged resides between c-ray source and detector. The term "gain correction (image)" is mainly used for 2D x-ray whereas in CT the term "air scan" may be used instead.

"Object image": is an image acquired of an object, that is, is acquired whilst the object does reside between c-ray source and detector.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
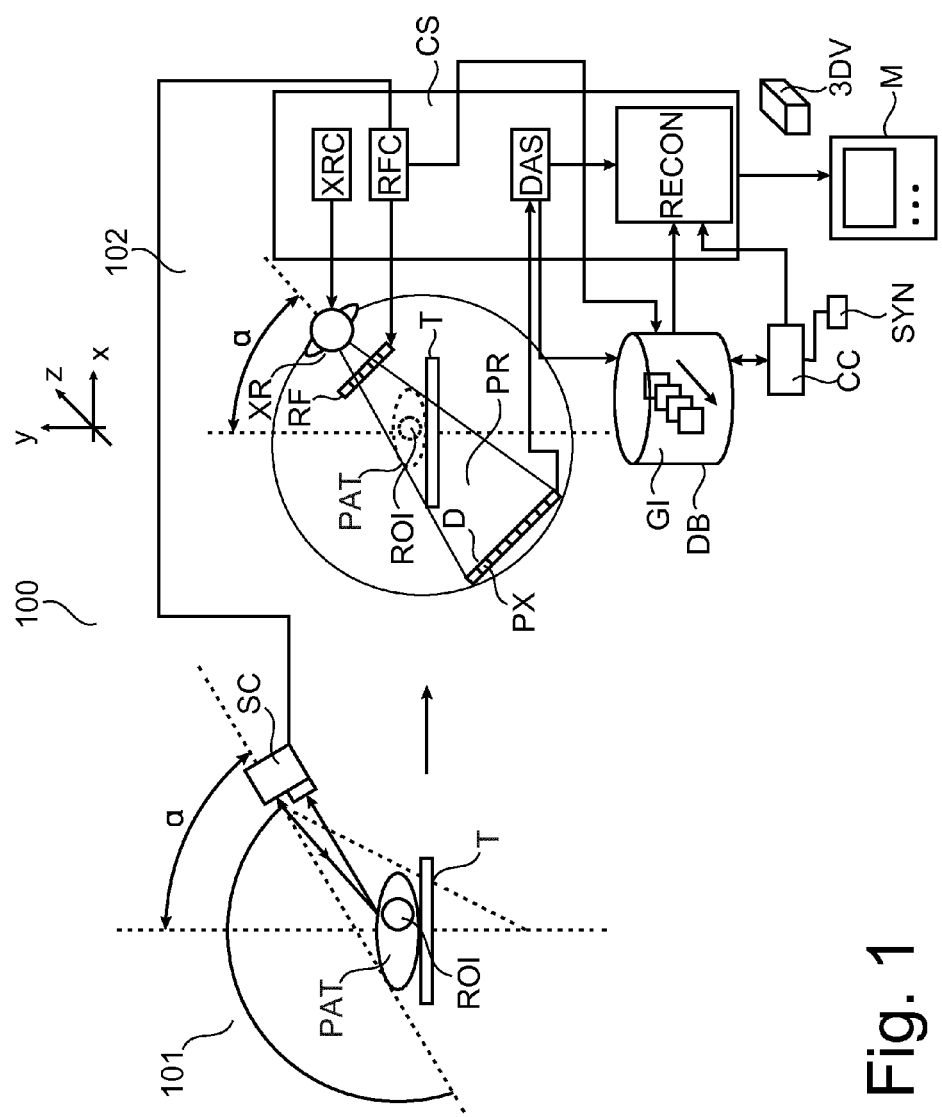
FIG. 1 shows an imaging arrangement.

FIG. 1 shows an imaging arrangement according to one embodiment. The arrangement 100 includes an internal imaging system 102 based on ionizing radiation and an object shape detector arrangement 101 whose operation is based on non-ionizing radiation.

The internal imager allows non-intrusively imaging the internals of an object PAT at a region of interest ROI whereas shape detector allows detecting the outer shape or silhouette of the either the whole object PAT or at least of the ROI.

In one embodiment, the imaging system 102 is a 3-D CT imager of the energy integrating or photon counting spectral type. In other, simpler embodiments, the imaging system 102 is envisaged as an interventional 2-D x-ray imager, in particular of the C-arm type.

When the imaging system 102 is a CT imager, its basic components include a frame (not shown) comprising a rigid, stationery gantry (not shown) and arranged therein a movable, in particular rotatable, (relative to the stationary gantry) rigid gantry (not shown) with a gantry opening. The rotating gantry rotates, during an imaging run, around an examination region (inside the opening) and about a longitudinal or z-axis. During an imaging run, at least the ROI of object PAT resides in the examination region.

A radiation source XR, such as an x-ray tube, is supported by the rotating gantry. Energized by a suitable actuator-controller arrangement in the imager system 102, source XR travels (in angular increments delta-theta) with the rotating gantry along a, in general, circular orbit about the examination region, whilst said tube emits a radiation beam (originating from a focal spot on the tubes anode) that traverses the examination region, and, in particular, traverses at least a region of interest ROI of the object PAT (hereinafter referred to as "the patient"). The beam PR is centered about an iso-center of the examination region and defines a generally circular shaped field of view to reconstruct for a transverse reconstruction plane, which is generally perpendicular to a center ray CR of the beam PR and which extends through the iso-center. There is also an x-ray tube XR controller XRC to control voltage and/or amperage within the tube to so effect beams with different energy spectra suitable for the imaging task at hand, for instance, the physiological particulars of the ROI.

A radiation sensitive detector array D is located opposite the radiation source XR, across the examination region to receive the radiation beam PR after its passage through the ROI tissue. Via operation of a DAS (data acquisition system), projection "raw data" is thereby generated that forms a projection image of the ROI along a current view $\theta$ as will be explained in more detail below with reference to FIG. 2. X-ray source XR is then rotated by a certain angular increment $\Delta\theta$ and the above measurements are repeated as the source XR travels on its orbit (usually a semi-circular arch or less), so that a sinogram is generated, i.e. the set of projection data obtained under each view $\theta$.

An object support T, such as a couch, supports object PAT in the examination region. Support T is energizable by a suitable actuator-controller arrangement to effect relative motion between couch and source XR to position object PAT/ROI with respect to x, y, and/or z axes before, during and/or after scanning. In particular, couch (and hence object PAT) is advanced along longitudinal z-axis (and inside the gantry opening) and the above sonogram measurements along the different view angles θ are repeated at each z position along axis until the desired width (in z-direction) of the ROI has been scanned.

The imager system 102 includes a reconstructor RECON which, for each z-position, reconstructs from the projection images associated with said z value, a slice image for each z. "Reconstruction" means solving for the tissue densities μ in equations (1), (2) below in the respective x,y plane (for each z). To this effect, a filtered back-projection algorithm or similar is used by the reconstructor RECON. The μ's in each slice are mapped onto suitable gray or color scale values in a palette. The mapped values can then be forwarded to a renderer that interacts with a video card to drive monitor M where the slice images may then be displayed. The slice image may also be stored in a database DB or otherwise post-processed. Each slice when rendered for display affords to the human viewer (such as clinician, hereinafter referred to as the "user") a cross-sectional view on the internals of the ROI at the z-position. The collection of slices together form a volumetric image data set 3DV indicative of the examination region, in particular, of the ROI therein.

A general purpose computing system WS ("work station") serves as an operator console, and includes an output monitor M and an input device such as a keyboard, mouse, and/or the like. Software resident on the console WS allows the user to control the operation of the system 102, for example, allows the user to set the tubes voltages/amperages and/or to control motion tube XR and/or couch T etc. directly or indirectly through selecting a pre-generated imaging protocol, or operation of reconstructor RECON.

Turning now to the shape detector arrangement 101, this includes a device SC having a non-ionizing radiation source (such as IR light or other) and a sensor for same. In one embodiment the shape detector arrangement 101 is rotatably arranged in a second frame (not shown) to allow rotation of said shape detector arrangement 101 around patient PAT in a manner similar to the X-ray source XR's orbit to so likewise afford different views along different directions θ. Shape detector 101's frame is preferably outside the imager 102's gantry but there are some embodiments envisaged, where the shape detector is integrated in the imager 102's gantry. The shape detector is used to detect the outer shape or relief (that is, the elevations of the of patent PAT's ROI when viewed along one of a plurality of desired views θ). However, the shape detector may not necessarily be rotatably arranged, and the different body shapes for each view may be inferred instead from one or more 3D images of the object acquired from a fixed position of shape detector 101. Also, in one embodiment, a 2D scout scan together with a suitable 3D patient model is used. In a CT 2D scout scan, a 2D projection x-ray image is acquired by moving the tube/detector across the patient without rotation. A very low dosage may be used (sub-Thz) or shape detector 101 is installed close to the x-ray tube and operates (instead of the x-ray tube) to sense the body shape whilst the tube XR moves as if performing the 2D scout scan. Non-ionizing radiation source ("projector") and sensor may (as schematically shown in FIG. 1) or may not be housed in the same housing.

In one embodiment said device SC is a ranging or (spatial) depth sensing camera. Examples are Microsoft Kinect or ASUS Xtion Pro Live equipment. According to one embodiment the sensor uses a pre-defined structured light pattern, projected onto the region of interest of patient PAT or object to be sensed. According to one embodiment the structured light pattern is a speckle pattern. According to one embodiment infrared light is used but using light in the visible spectrum is also envisaged. The camera supplies 3D depth data information, that is, spatial depth information that maps out object PAT's outer surface. According to one embodiment, range camera RC includes a projector that projects a cone of structured light onto patient PAT, or at least onto ROI. Said structured light may for example be formed as a "speckle" pattern as described in US 2009/0096783. The reflection of said light from the patient's surface back to the camera is then registered by the camera's sensor SC. The "distortion" in the reflected speckle pattern is registered by the sensor and a processor compares this with how the speckle pattern ought to have looked like had the pattern been projected onto a flat (reference) surface at a predefined distance. The registered distortions are then translated into a distance value for each pixel. In this embodiment, camera SC outputs the desired shape specification in form or a depth image, that is, as an array of depth values with each value measuring a distance of a respective point on the object's PAT surface. It is understood that the above described speckle pattern implementation is but one embodiment and that the range camera SC may also operate according to alternative principles, for example time-of-flight, stereo triangulation, sheet of light triangulation, interferometry and coded aperture and so on. Control of the shape detector 101 and its interaction with internal imager 102 is effected by suitable software modules resident on work station. Interaction with internal imager 102 will be explained in more detail below with reference to FIG. 2.

Figure 2:
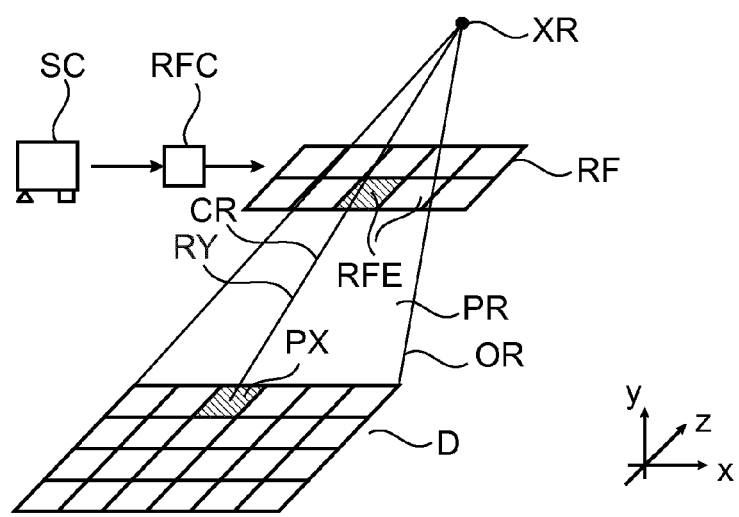
FIG. 2 shows operation of a beam shaper as used in the imaging arrangement of FIG. 1.

As schematically shown in FIG. 2, detector array D includes one or more rows of individual detector pixels PX that each respond to an individual radiation ray RY of the beam PR. Specifically, the response at each cell is in the form of an electrical signal that is in general proportional to the intensity (or energy flux) of (or in) the ray RY. The intensity, or energy flux, in respective portions of the beam is in turn a function of their previous attenuation that the rays in those portions experienced in their passage through the object PAT tissue.

The photon flux (for a certain energy) "seen" at a pixel PX is in sufficient approximation governed by the Beer-Lambert law which, for inhomogeneous materials in the ROI can be written in integral form as:

$$\frac{I}{I_0} = e^{-\int_L \mu(s) ds} \tag{1}$$

where $I_0$ is the (initial) intensity (energy) of the (patient) incident ray RY and I is the energy deposited and registered at the respective detector cell PX after said ray RY has travelled along an in-tissue path length x. $\mu(s)$ is the attenuation coefficient that varies with in tissue-path length L of ray RY.

For the total energy in the beam PR, the above equation (1) is integrated over the energy spectrum of the beam and can be written:

$$\int_0^{E_{max}} E \cdot S(E) e^{-\int_L \mu(s) ds} dE \tag{2}$$

Equation (2) is relevant for conventional, energy-integrating CT but is not used for photon counting spectral CT, where the relevant quantity is the number of counts in an energy bin. Therefore, in the photon counting embodiment, the factor "E" omitted, and the integration is not over the full energy range, but only over a given energy interval for the respective bin.

At least one pre-filter RF ("beam shaper") is located between the examination region in the path of the beam PR. The beam shaper RF is a physical device with a filter body that pre-attenuates the beam, that is attenuates portions of the beam before interaction with object PAT tissue. As described in greater detail below, in one instance, the beam shaper attenuates the beam PR to achieve an approximately same predetermined x-ray flux profile "(beam) energy profile") across the detector pixels PX of the detector array 520 at each angle of rotation θ. This allows for compensating for no or low attenuation at peripheral regions of the scanned subject or object (or high flux regions) while providing angular independent homogenization of the x-ray flux detected by the detector pixels. The filter RF's body is made up from a number of individual filter elements RFE that in one embodiment are each addressable to locally affect the attenuation strength. As can be seen there is a natural association between filter elements RFE and pixels PX, namely between the pixel PX that "sees" or registers the ray RY pre-attenuated by a respective one of the filter elements.

In other words, beam shaper RF is configured to "shape" a transmission profile of the beam 310. In one embodiment, the beam shaper RF shapes the energy profile of the emitted radiation so that transmission is greater nearer a central ray CR of the beam PR and decreases in a direction away from the ray CR and towards outer rays OR although more general beam shapes are envisaged herein as explained in more detail below. Beam shaper RF can be used in place of or in combination with a conventional bow-tie filter.

The filter controller RFC operates to vary the energy profile (linearly or non-linearly, in a deterministic or locally random but overall defined manner) along portions of the beam PR in a single dimension, for example, along the x-direction, or in multiple dimensions, for example, along the x-z plane. In other words, pre-filter controller RFC interacts with pre-filter RF so that the different intensity profiles of the beam PR can be effected. For instance, in one embodiment the local densities within the filter body can be changed as specified by the controller RFC, for instance by a specification of the density distribution in the filter body. In one embodiment, the filter's body is "freely formable" so as to adapt the intensity profile individually to any object PAT shape and its various projective "footprints" or appearances under different views θ. Examples are in Applicant's WO2013001386 or U.S. Pat. No. 6,453,013. A purely mechanical example of a pre-filter that affords a slightly lower level of shape adaptability is a beam shaper with movable sheets (for instance from metal or similar) or similar components that can be stacked up or otherwise superposed in a plurality of layers to increase attenuation intensity.

Operation of beam shaper RF (or "pre-filter", both terms are used interchangeably herein) as used herein may be distinguished from other types of filters frequently used in imaging system, namely collimators, that are sometimes likewise referred to as "beam shapers". Collimators include an aperture to shape the geometry of the beam (pyramidal, circular conical etc) by completely blocking out portions of the beam and letting other portions pass without any filtering (or some degree of filtering by semitransparent wedge filters) to adapt the beam's cross-section to the shape of the ROI so that, ideally, the cross-section of the beam passing through the ROI is essentially coextensive with the ROI when viewed under a current view. The instant beam shaper RF as used herein however is primarily concerned with shaping the energy profile across the propagation direction of the beam without regard to the size of the beam's cross-section when passing through the ROI. In one embodiment, the instant beam shaper is indeed used in combination with a collimator. In this embodiment the collimator is arranged between x-ray source and beam shaper RF so that the beam shaper acts on the collimated beam. There are also other embodiments envisaged, in which the two beam shaper functionalities are integrated into one device.

The pre-filter as used herein is dynamic in the sense that it allows adapting the energy profile to the individual shape of the ROI for each view θ. In particular, the density or material distribution of the filter body that causes the pre-attenuation is adjusted so that it varies essentially inversely with the shape of the patient for each view θ, that is with the individual in-tissue path lengths through the ROI along a view θ: The attenuation is low in beam portions that head for ROI portions where more tissue is expected and is high in beam portions that head for RPI portions where less tissue is expected. In one embodiment, the energy profile of the beam PR is adapted in response to the depth image supplied by shaped detector 101 per view θ. That is, the filter RF is dynamically adjusted in concert with the X-ray tube XR's orbiting so that the energy profile of the beam can be adjusted to the apparent change of the ROI shape caused by the changing spatial views θ on the ROI.

The advantage of having a beam shaper RF that is individually adjusted to not only the individual patient but also to the various views thereon, adds a layer of complexity when it comes to calibration. Calibration is the task of determining the quantity $I_0$ denominator in equation (1), that is, the intensity of the incident beam without the object PAT. Only when the denominator $I_0$ is known is a truthful reconstruction possible. One example of a calibration protocol is to take two measurements of the detector D's response: (i) when the patient does reside in the examination region (this is the actual imaging run) and (ii) when the patient does not. In other words an "air scan" is taken either before the imaging run (that is, when the patient resides in the examination region) or thereafter. Because the beam shaper's settings are adapted with each patient and view to effect the "bespoken" beam energy profiles, a single air scan is no longer sufficient. In one embodiment, it is proposed to execute a multi-air scan instead, that is, to acquire a gain image for each view, while the filter RF changes its profile depending on the view. "Gain image" as used herein is understood to indicate the measurement registered by the detector D when no patient resides in the examination region. The arrangement of FIG. 1 as proposed herein therefore includes a calibration controller CC that is configured to run said multi-view (θ) air scan calibration protocol. In one embodiment, controller CC, and beam shaper controller RC run as modules on work station WS.

Operation of controller CC according to one embodiment will now be explained with reference to the flowchart in FIG. 3.

At step S305, the patient's shape is determined by operation of shape detector 102. In one embodiment, shape detector 101 rotates around the patient in the same manner as the tube XR in the internal imager 102 would (or indeed does in one embodiment) and acquires for each view θ a respective depth image. In other embodiment, a single depth image is recorded from a fixed position and this image is then converted by use of 3d model of the patient into the depth images for the respective views. Preferably, it is ensured patient PAT lies on couch T in same posture which patient would assume when lying in the gantry during X-ray irradiation in the internal imager 102. This ensures that both phases (that is, shape detection and calibration) can proceed on substantially the same body contour.

For each of view θ, the respective depth image is forwarded via suitable camera CS interface and is then received in step S310 at filter controller RFC of internal imager 102. Filter controller RFC then operates to adjust at step S315 the dynamic beam shaper RF's settings in response to the body shape as recorded in the depth image. In particular, the depth values of depth image can be translated into in-tissue path lengths that the XR beam will need to pass to meet the respective pixel PX position. The filter element RFE associated with said pixel PX is then inversely adjusted to the respective depth value. In other words, said element RFE is modified so as to produce a higher attenuation when in-tissue path length associated with said pixel is small and, accordingly, is modified so as to produce a lower attenuation when in-tissue path length associated with said pixel is large.

In step S320 the multi-view air scan is then acquired with the patient being placed on the couch, but outside the CT gantry. Again, the pre-filter RF is adjusted in dependence on the depth values as generated in step S305.

In one embodiment, during execution of steps S305, S320, internal imager's 102 gantry (with tube XR) will appear to an onlooker as if rotating "simultaneously" with the rotation of the shape detector SC around the patient during the multi-view air scan without the patient residing between tube XR and detector D. Whilst patient PAT is outside the gantry, the gantry opening is properly shielded so that no radiation escapes and is incident on patient PAT. The motion of shape detector SC and tube XR are in step and synchronized with the view θ so that, at each, instance during execution of steps S305, S320, the same views are assumed by shape detector SC and tube XR, respectively. In other embodiments however, an interlaced synchronization of the shape detector SC and tube XR motion along their respective orbits are also envisaged. In other embodiments, it is first the complete set of depth images that are acquired and then the gain images. In either case, the depth images and gain images are stamped by the respective view so they can be matched up according to the views later. The gain images are then stored in a Database DB or other memory in association with the respective views θ under which they have been acquired.

The optical measurement system 101 is configured to scan the entire ROI of the patient that is to be imaged, over width of the relevant-axis, to ensure all required slices can be reconstructed. For cone-beam CT, the dynamic beam shaper needs to be adjusted to effect profiles, which serve all the required slices along the z-axis at the same time so that it suffices to run a single multi-view air scan on the basis of the acquired patient slices.

For cone beam imagers, it has been found that good calibration results can be achieved when avoiding transition zones of the object where a sudden change in shape type occurs, for instance, at the hips where the torso transitions into the legs. The cross-sectional shape type changes from elliptic to a double circular one. Rather than straddling the transition zone, it is best to calibrate separately for the torso region and then for the leg region.

At step S325, after the "multi-view" air scan has been accomplished, couch T with the patient PAT is moved into the gantry and the object PAT projection images (on which the reconstructor RECON is to operate to generate the actual slice images) with the patient PAT between tube and detector are then acquired in the imaging run. It is also envisaged in one embodiment, to acquire the object images (that is, the projection images of the patent PAT) first and then do the multi-view air scan thereafter although, in a preferred embodiment.

At step S330, one or more of the slice images are then reconstructed by using, for each view and each slice (z-position), the corresponding air-scan coefficients $I_0$ (as derivable by logarithmic scaling of the respective gain image) and the object PAT sinogram acquired when the patient resided between tube and detector as per step S325.

In an alternative embodiment to step S305, a number of filter RF settings are defined beforehand, in a preparatory pre-calibration phase, such that there is at least one that fits any given patient cross-section. This can be established by using statistical data of body shapes. The different filter profiles (and the respective beam shaper settings) can then be assigned to age groups, sex, physique (for instance by using categories: slender, medium, stocky), etc. The different filter profiles may then be stored in association with the respective body shape and view θ (that is, the shape as it would appear under each view θ) in database DB. In other words, the different filter profiles are associated with the respective view θ.

After the pre-calibration phase, in the actual calibration phase, the body shape of an instant patient is then supplied, in a preferred embodiment by a simple user specification, and the so specified body shape characteristic is then used to query database DB. In response to this query, the (dynamic) beam shaper profile setting is retrieved, which best fits the obtained patient's shape characteristic for each view, and the "multi-view air calibration" is then done using the so selected beam shaper profile as per step S325 above. To establish the fit between pre-stored setting and body shape specification, any suitable criteria can be used for quantifying the "distance" between the profile of depth image and the gain image associated with the respective pre-stored filter settings. In other words, in this alternate embodiment, no measuring of the current patient shape with the shape detector 102 in step S305 is necessary. Instead, the user may be presented with a suitable user interface with input means for the user to select the appropriate patient shape best describing the current patient. In a variation to this embodiment however, the shape detector SC arrangement may still be used instead of the user interaction to supply the body shape characteristic that is used to retrieve the best fitting one from the pres-stored filter RF settings. For instance a graphical user interface may include graphical icons each depicting diagrammatically the various body shapes. The user then clicks by means of a pointer tool (finger touch action is also envisaged in a touch screen embodiment) on the respective icons. In response to the selection or measurement of the body shape, the filter setting associated with the respective view θ (on said body shape) is then retrieved and applied to the pre-filter RF in imager 102. The imager 102 is then ready for the calibration phase and the multi-view air scan calibration as per step S320 can then commence as previously described.

The multi-view air calibration may be done at the beginning of a working day (or, less frequent, once a week/month, etc.) for all different beam shaper profiles (or, if known beforehand, for a selection of patients that are slated for an imaging session on that day), and/or the respective gain images are then stored in database DB in association with the respective patient body shape characteristics and view θ. Depending on the current patient to be imaged in given run, the imaging session is carried out with the respective beam shaper profile as used previously for the calibration. The corresponding calibration data (that is, the gain images per slice position z and view θ) are then loaded into the reconstructor RECON (the reconstructor or an image protocol scheduler run by work station WS may issue a respective request for same) and the loaded gain images are then applied in the reconstruction step.

Figure 4:
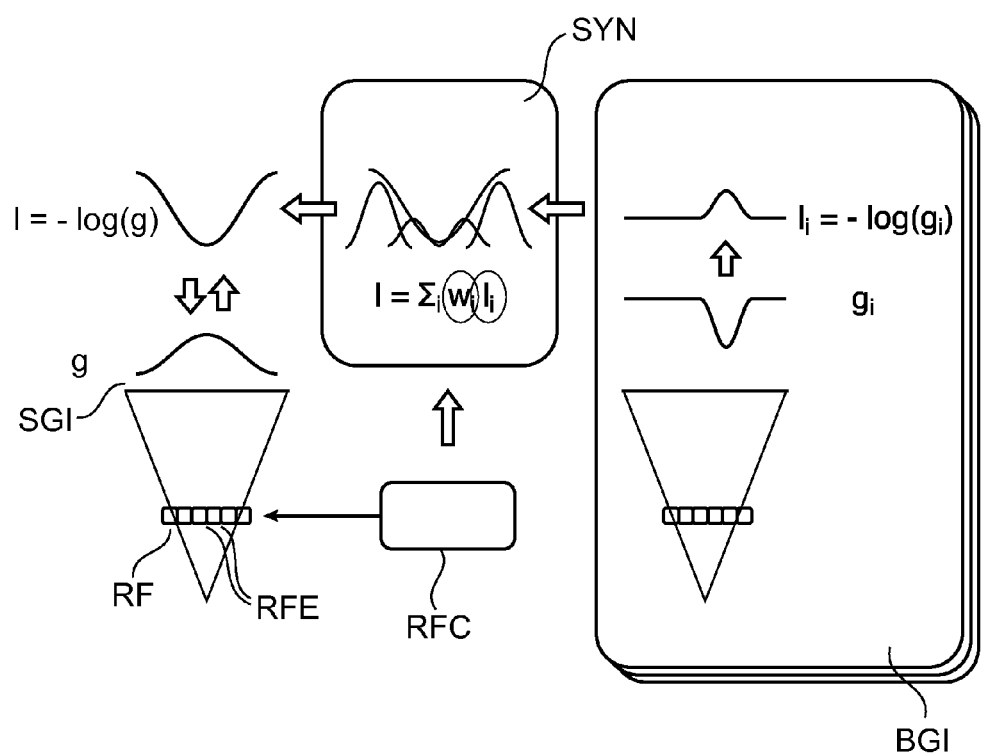
FIG. 4 shows a basic block diagram of a further calibration method according to a second embodiment.

Reference is now made to the schematic block diagram of FIG. 4, where the basic principle of a further calibration method is shown.

In this embodiment, the calibration controller CC includes a gain image synthesizer SYN. It is proposed herein to synthesize the gain map from a sum of weighted line integral images of a set of basis gain images recorded in a plurality of air scans whilst applying in air scan to the pre-filter RF, in turn, each of a set of basis filter configurations or settings. The weights are determined by querying the respective target configuration of a pre-filter RF setting that is to be sued for an imaging run of an instant patient. In one embodiment, the filter body of pre-filter RF is assumed to be made up of filter elements that are individually addressable by the controller RFC so as to act together or individually to effect a localized attenuation pattern, for instance, a pointwise attenuation action on ray RY when passing through the filter body at said filter element. One way to achieve this is to effect pointwise or localized changes of the material density distribution in the filter body at that point or by changing the material distribution in the filter body at that point. In one embodiment the material distribution is changed by locally "stacking up" the filter element at a given point to increase attenuation or by rearranging the filter elements so that fewer elements are superposed so as to decrease the attenuation action at that point.

In one embodiment, the filter body is formed from an array of "tubelets" (with their longitudinal axis arranged along the x-ray tube XR—detector D axis), that can each be filled with a suitable attenuating liquid at different levels. The controller RFC acts to selectively change the filling heights for one, or a group of or all tubes (by pumping liquid into or draining liquid from the respective tube or tubes) to point-wisely control attenuation. The array (that is, the filter body) can be shifted (by a suitable actuator-controller arrangement) so as to align as desired each tubelet or groups of tubelets with the X-ray source's XR focal point. An example of such a fluid beam shaping device similar is briefly mentioned above and is described in Applicant's U.S. Pat. No. 6,453,013. Each filter setting (or "configuration") is specified by the fill level in each tube, in other words, a filter setting is completely determined by a matrix having one entry for each tube in the array, each entry being a numerical code (for instance height in mm or similar) for defining a fill level of that tube. This matrix can be used to specify a pre-filter setting for the pre-filter RF. The matrix describes an "attenuation pattern", that is, it describes which ones of the filter elements is activated/not activated. An activated filter element will cause attenuation whereas a de-activated one would not. If there is an entry in the matrix then the respective filter element is to be activated and the entry itself describes the individual attenuation strength of the activated ones of the attenuation elements.

Broadly, in the FIG. 4 embodiment, a "base attenuation profiles" or base gain images for certain basis filter configurations are measured in an offline calibration procedure, that is, said basis profile measurements occur in the pre-calibration phase prior to an actual calibration phase. Thus, there is no need for intermediate calibration acquisitions for each patient scan. In said offline calibration procedure the set of base gain profiles for a predefined list of base beam shaper attenuation settings is acquired. The basis set includes a "clean" scan where no local attenuator element is activated, that is, the radiation is registered as supplied by the tube (the attenuation caused by air interference can be neglected for present purposes). In the subsequent online phase there is a synthesis step performed by gain image synthesizer SYN where the beam shaper attenuation profile SGI ("target gain image" or "final gain image") that is required for the instant patient PAT (for whom an imaging run is to commence) is synthesized from the pre-stored base gain images profiles BGI and the required attenuation pattern ("target filter setting or configuration") that need to be applied to the pe-filter RF for the instant patient's body shape (or view θ thereon) in an imaging run. In other words, this embodiment harnesses the superposition property of line integrals to compose the target gain image SGI from i) a set of base gain images BGI held in database DB and ii) a specification of the target attenuator setting as required for the instant body shape (and/or view θ thereon) of the instant patient PAT. The superposition property mentioned above is harnessed by forming a linear combination of the basis images BGI. The linear combinability means in particular that i) adding up (pixel-wisely and after logarithmic scaling) a collection of those basis gain images BGI that allow replicating the attenuation pattern of the target attenuation setting and ii) linearly scaling up or down the attenuation strength (or intensity) of each filter element in the basis images of said collection to the respective attenuation strengths as required by the respective attenuation strength in the target filter setting. However the later linearity in respect of attenuation strength scaling applies with accuracy only for those basis gain images whose filter elements are aligned with the x-ray source when the object image is taken. The non-aligned filter elements will inevitably cast an x-ray shadow on the detector and changing the attenuation strength of the filter element will not only lead to a corresponding change in line integral in the direct line of sight, but also vary the local extent of the attenuated detector region. To account for this, multiple basis images may be used per filter element as will be explained in more detail in relation to FIG. 5.

In FIG. 4, $g_i$ indicates the attenuation profile as recorded in the respective gain image BGI and $l_i$ is the energy intensity profile obtained from $g_i$ by logarithmic scaling. A similar notation is used for the target gain image SGI on the left hand side of FIG. 4. The attenuation profiles and the line integrals are shown here a 1D profile curves but it is understood that in general the respective profiles as 2D surfaces when the filter is adjustable across two dimensions as preferred herein.

Figure 5:
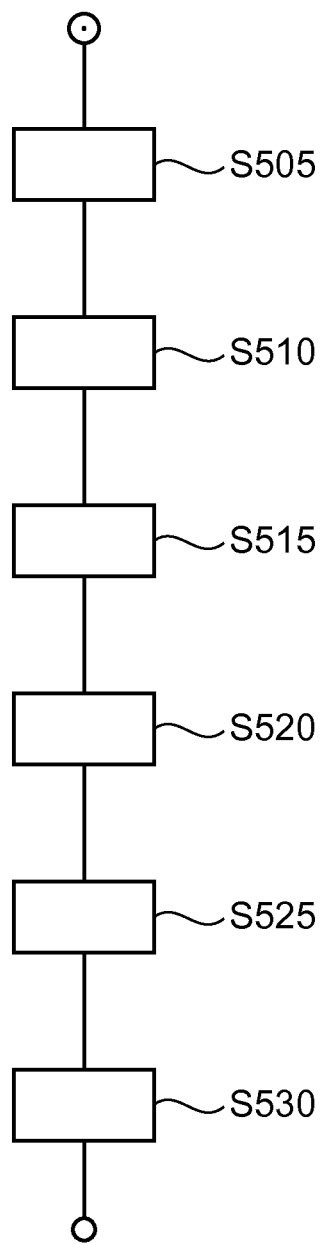
FIG. 5 shows a flow chart of the calibration method of FIG. 4.

The method of FIG. 4 is now explained in more detail with reference to the flowchart FIG. 5 detailing the steps performed by calibration controller CC.

During the (offline) pre-calibration procedure, the basis gain images BGI are acquired in step S505 for a set of predefined "basis" filter settings, For instance, in the previously mentioned dynamic fluid beam filter, the filter settings correspond to certain filling levels of the tubeletss. Although in the following the method is explained by reference to said fluid beam filter with the understanding that this is merely one embodiment and other alternative beam filters with for instance addressable mechanical elements such as sheets to tabs formed from metallic (or other attenuating material) are also envisaged herein.

The set of the basis calibration filter settings is chosen so that during the subsequent imaging run substantially every beam shaper attenuation configuration (or, equivalently, every required target gain image SGI) of interest can be composed or synthesized by a weighted sum of the calibration settings (or, equivalently, from pre-stored basis gain images BGI). In mathematical terms, the set of calibration configurations (or basis gain images BGI) forms a basis and therefore span a "vector space" for all beam shaper configurations (or target gain images SGI) that can be reasonably expected to be required in the future There is a natural association between the basis filter configuration and the basis gain images BGI themselves. The later can be reproduced by applying the earlier to the imager 102's pre-filter RF in the pre-calibration procedure.

In one embodiment, the set of basis (calibration) filter settings comprises a filter setting where only a single beam attenuator element is activated, that is, it is only said singly activated filter element that causes the x-ray attenuation—the remaining filter elements cause no attenuation or only negligible attenuation. In other words, and as shown in FIG. 4, the associated basis gain images BGI have localized single valley or "dip" profiles and the corresponding line integral is a single peak function. However alternative options to construct the basis gain images are also envisaged herein. For instance rather than activating a single filter element at the desired position, a group of adjacent filter elements may be activated together instead. This would result in a "coarser" basis of basis gain images (as compared to recording the base images with only a single element active) which may allow saving memory space and CPU time. The basis gain images and/or a specification of their associated basis filter configurations are then stored in database DB. However other basis filter configurations/basis images are also envisaged with a spread out attenuation pattern. The different basis filter configurations are so chosen that substantially any given attenuation pattern of a target pattern can be composed from the basis images or basis filter configurations. Similar to step S310 above, a specification of the body shape for the instant patient at a given view θ is received. The previously introduced shape detector 101 may be used for this effect, but there are other embodiments envisaged where no shape detector 101 is used but the user simply selects by means of a suitable user interface an at least rough estimate of the expected body shape in the imaging run.

Figure 3:
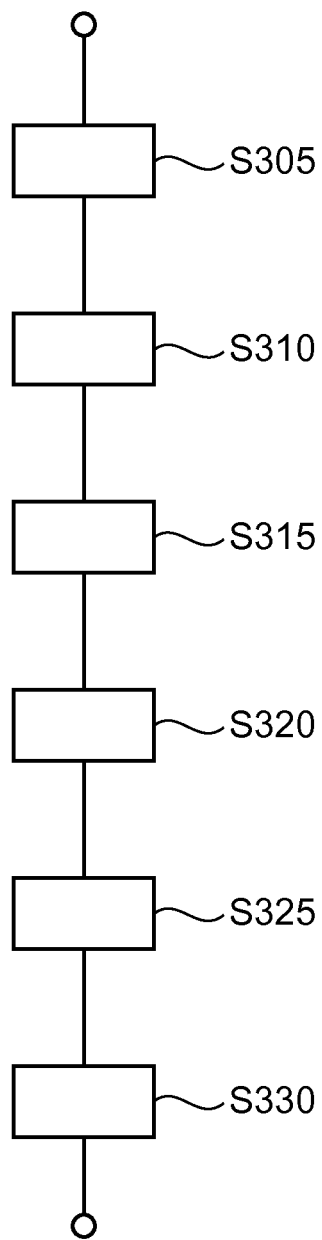
FIG. 3 shows a flowchart of a calibration method according to a first embodiment.

In step S515, the instant body shape specification is then translated, as previously described in FIG. 3, into the target filter configuration whose local attenuation action or strength is inverse to the respective in tissue path length or thickness as recorded in the body shape specification. The beam shaper configuration is either computed on the fly from the body shape specification or is retrieved from database DB where different body shape specifications are held, each in association with a correspondingly fitting beam shaper configuration. The above inverse relationship between attenuation and in-tissue path length may not necessarily be "inverse" in the strict mathematical sense because other constraints may likewise be taken into consideration, for instance avoiding too steep transition areas that may compromise accuracy of the gain calibration.

In step S520, the beam shaper configuration as established in step S515 is then decomposed into a set of the basis single filter element configurations as shown schematically in FIG. 4. This step S520 is preferably carried out during the imaging run but may also be carried out beforehand if the patient/patient shape is known. The previously, in step S505, recorded basis gain images BGI into which the to-be-applied target filter configuration has been decomposed into, are then retrieved from database DB.

The retrieved basis gain images BGI are then converted into line-integrals using the clean gain image as a normalizer (See an example in below table in the upper left hand entry). The line integrals of the basis gain images are then corrected for beam hardening, which then allows their superposition.

In step S525, the target gain image (line-integral) is then synthesized or computed as the weighted sum of the beam-hardening corrected line integrals from the basis gain images as retrieved.

In step S530 (similar to step S330 above), the target gain image is the used in the reconstruction algorithm once the sinogram of the instant patient are acquired in the imaging run by internal imager 102.

Since the material composition of the attenuator body (for instance, the liquid with which the tubelets are filled) is known, a beam hardening compensation of the line integrals can be applied. Because of the beam hardening compensation, the weights can be determined for each point by linearly scaling the respective single attenuation intensity of a single basis gain image to the attenuation intensity as required by the target filter configuration at the respective point.

In the tubelet filter embodiment, in the simple case of tubelets that are assumed aligned with the x-ray focus, the weights represent the linear scaling up or down of to the respective filter element attenuation strength at the aligned filter element to the respective attenuation strength in the target filter configuration, For instance, if the filling level height required by the target filter setting is twice that of the filling level height of the aligned filter element of one of the basis filter stetting, then the associated basis image will receive a weight of 2 in the linear combination of the synthesis. In this case, a filling level twice the height will locally increase the measured line integral likewise by a factor 2, after beam hardening has been compensated for. In the more general case the weights can be derived, that is interpolated, from various attenuator settings recorded in a calibration look-up-table.

In the most general case, that is, when a tube is not aligned with the x-ray source's XR focus), the spatial reach of the x-ray shadow that is caused by a single attenuator element depends on the attenuation level. To account for this, for each attenuation element, several basis gain maps are acquired for different attenuation levels, e.g. fill level heights, and the calibration table is expanded by adding a further "dimension" that reflects the fill level height. Instead of weighting the measured line integral in the superposition/synthesizing step, the best fitting configuration from the table is selected by interpolation. Example: If there are two attenuation levels a and b in the basis gain images $g_a$, $g_b$, and level c needs to synthesized, with a<c<b, linear interpolation may be used: $g_c=(c-a)*g_a+(b-c)*g_b$. In this case the weights are (c−a) and (b−c) for the respective gain images $g_a, g_b$. Another option is to restrict the possible filter configurations, e.g. to either use gain image $g_a$ or gain image $g_b$. In the latter case, the weights are a token for this restriction and degenerate into binary ("1" or "0") weights.

Since the attenuation material is known, standard approaches for beam hardening compensation can be applied before adding the (weighted) line integrals. In one embodiment, a specification or at least a model for the X-ray source spectrum without beam shaper is used. One approach may reside in the conversion or transformation of the measured line integrals in the basis images BGI into a fictitious "mono-energetic" line integral using the tube model/specification and the known material properties of the beam shaper absorption material. These mono-energetic line integrals can then be simply added and finally converted back to the corresponding line integral of the actually applied spectrum. The line integral conversion can be done by text book methods for beam hardening compensation, e.g. Look-up-table LUT or a correction polynomial. The LUT relates "true" material thickness vs. measured material thickness for a given input spectrum (the later affected by beam hardening). For a spectral resolving detector D, the procedure has to be applied to each energy bin or energy channel separately.

It will be understood from the above, that the calibration method according to FIGS. 4/5 can also be beneficially used for calibrating a 2-D X-ray apparatus such as a C-arm interventional scanner or conventional 2D radiography. In this embodiment there is in general a single (or a very few) view(s) along which one or more projection images are acquired and there is no reconstruction step. In this embodiment, it is the projection image that forms the final output and is rendered for display on screen M. However in other embodiments, the synthesizing calibration method of FIG. 4/5 is used in a CT context and is applied for each view θ separately.

If imager 102 is indeed a CT scanner, it can be any one of a first, second, third or fourth generation scanner.

It will be understood herein, that the x-ray detector D can be either photon counting or integrating. Photon-counting detectors measure each individual x-ray photon separately, while integrating detectors measure the total amount of energy deposited at the detector pixels. In spectral CT, the pixels are configured to count only photons in a certain energy range, or even measure the energy of each absorbed photon.

The controller CC may be arranged as a dedicated FPGA or as hardwired standalone chips. In one embodiment, the controller CC is resident on work station WS running thereon as one or more software routine. The controller CC may be programmed in a suitable scientific computing platform such as Matlab® or Simulink® and then translated into C++ or C routines maintained in a library and linked when called on by work station WS.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A calibration method for an imager having an adjustable filter arranged between a radiation source of the imager and a detector of the imager, the filter suitable to effect, by adjustment of the filter's setting, different non-homogenous energy intensity profiles of a radiation beam generated by the radiation source before passage of said beam through an object to be imaged, the method comprising:
  adjusting the filter for a plurality of different basis filter settings, one at a time;
  acquiring at the imager's detector a plurality of basis gain images, at least one gain image for each of the different filter settings; and
  synthesizing a target gain image from the one or more of the plurality of gain images, wherein the synthesizing step includes forming a linear combination from one or more of the plurality of basis gain images, wherein the linear combination involves weights each weight representing an individual attenuation strength of a respective ones of filter elements of the filter.

2. Method of claim 1, wherein each of the basis gain images record a different attenuation profile that is caused by a respective, locally restricted attenuation of the adjustable filter.

3. The method of claim 2, wherein the attenuation profile as recorded in each gain image is a different single-dip profile.

4. The method of claim 2, wherein the filter elements are individually addressable to effect an essentially pointwise or at least localized pre-attenuation of the beam, wherein the single dip attenuation profiles each correspond to an attenuation of a respective one of the filter elements.

5. The method of claim 1, wherein the step of synthesizing the target gain image is executed in response to receiving a shape specification of an object to be imaged.

6. A calibration method for an imager having an adjustable filter arranged between a radiation source of the imager and a detector of the imager, the filter suitable to effect, by adjustment of the filter's setting, different non-homogenous energy intensity profiles of a radiation beam generated by the radiation source before passage of said beam through an object to be imaged, the method comprising:

receiving at least one specification of a shape of the object;

adjusting the filter for a plurality of different filter settings, one at a time;

acquiring at the imager's detector a plurality of gain images, at least one gain image for each of the different filter settings, wherein the imager's x-ray source is rotatable about an examination region, wherein each of the gain images are acquired at different views with the filter setting adjusted at step in dependence on the different views and/or the received object shape specification.

7. The method of claim 6, further comprising the step of:
optically scanning the object to obtain the object shape specification received at step.

8. The method of claim 6, wherein the different filter settings are pre-stored in a database and wherein the adjustment step includes selecting for each view a filter setting from said pre-stored filter settings, each pre-stored filter stetting associated with the respective view on the object shape, the selection being dependent on the received object shape specification and/or view and/or wherein the plurality of detector gain images are stored in a gain image repository.

9. The method of claim 6, wherein the scanning step and the gain image acquiring step is synchronized with the respective view.

10. An imager calibrated according to the method of claim 1.

11. The imager of claim 10, wherein the imager is a 3D CT imager or a 2D X-ray imager, in particular, an interventional 2D X-ray imager of the C-arm type.

12. An imaging system including an imager and a calibration controller configured to carry out the method steps according to claim 1.

13. An imaging system including an imager and a calibration controller configured to carry out the method steps according to claim 5, further including an optical scanner for supplying the shape specification of the object.

* * * * *